United States Patent [19]

Wingen et al.

[11] Patent Number: 4,619,885
[45] Date of Patent: Oct. 28, 1986

[54] PHOTOPOLYMERIZABLE COMPOSITION COMPRISING A 1,3,10-TRIAZAANTHRACEN-4-ONE AS THE PHOTOINITIATOR

[75] Inventors: Rainer Wingen, Frankfurt; Ulrich Geissler, Hochheim am Main; Hans Ruckert, Wiesbaden-Naurod, all of Fed. Rep. of Germany

[73] Assignee: Hoechst Aktiengesellschaft, Frankfurt am Main, Fed. Rep. of Germany

[21] Appl. No.: 739,512

[22] Filed: May 31, 1985

[30] Foreign Application Priority Data

Jun. 1, 1984 [DE] Fed. Rep. of Germany ....... 3420425

[51] Int. Cl.$^4$ .......................... G03C 1/68; G03C 1/76
[52] U.S. Cl. .................................... 430/260; 430/263; 430/281; 430/288; 430/285; 430/920; 430/271; 430/275; 430/278; 522/63; 522/121
[58] Field of Search ................. 522/63, 121; 430/281, 430/288, 285, 920, 271, 275, 278, 260, 263

[56] References Cited

U.S. PATENT DOCUMENTS

| | | | |
|---|---|---|---|
| 3,765,898 | 10/1973 | Bauer et al. | 430/920 |
| 4,464,457 | 8/1984 | Bosse et al. | 522/63 X |
| 4,465,758 | 8/1984 | Wingen et al. | 430/288 |
| 4,496,646 | 1/1985 | Ito | 430/281 X |
| 4,504,573 | 3/1985 | Ishikawa et al. | 430/281 X |

FOREIGN PATENT DOCUMENTS

| | | |
|---|---|---|
| 3233604 | 3/1984 | Fed. Rep. of Germany . |
| 1354541 | 5/1974 | United Kingdom . |

Primary Examiner—John E. Kittle
Assistant Examiner—Cynthia Hamilton
Attorney, Agent, or Firm—Schwartz, Jeffery, Schwaab, Mack, Blumenthal & Evans

[57] ABSTRACT

A photopolymerizable composition is disclosed which comprises (a) a polymeric binder, (b) a polymerizable compound, and (c) a photoinitiator comprised of a compound according to formula I

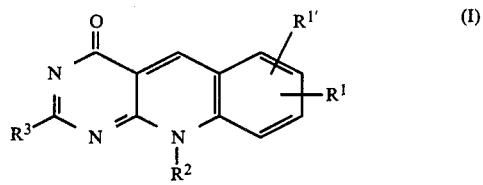

wherein
  $R^1$ is a hydrogen atom, a halogen atom, an alkyl group, alkoxy group, or dialkylamino group,
  $R^{1'}$ is a hydrogen atom, a halogen atom or an alkyl group
  $R^2$ is an alkyl group or an alkoxycarbonylalkyl group, or, if $R^1$ and $R^2$ each denote an alkyl moiety,
  $R^1$ and $R^2$ together form a five- or six-membered ring, and
  $R^3$ denotes a tertiary amino group.

The compounds are distinguished by their good solubility and high activity in the short-wave visible region of the spectrum.

14 Claims, No Drawings

PHOTOPOLYMERIZABLE COMPOSITION COMPRISING A 1,3,10-TRIAZAANTHRACEN-4-ONE AS THE PHOTOINITIATOR

BACKGROUND OF THE INVENTION

The present invention relates to a photopolymerizable composition comprising (a) a polymeric binder, (b) a polymerizable compound containing at least two terminal ethylenically unsaturated groups and having a boiling point above 100° C., and (c) a 1,3,10-triazaanthracen-4-one as the photoinitiator.

Photopolymerizable compositions which contain the components (a) and (b) and a polynuclear heterocyclic compound as the photoinitiator are known. In German Patent No. 2,027,467 (equivalent to British Patent Specification No. 1,354,541), specific derivatives of acridine and phenazine are described as initiators. German Patent No. 2,039,861 (equivalent to U.S. Pat. No. 3,765,898) discloses similar compositions containing quinoxaline derivatives or quinazoline derivatives as initiators.

All these compounds act as excellent initiators when they are irradiated with actinic light, particularly from light sources emitting in the near ultraviolet region. However, they are not optimally adapted to light sources which have an increased emission in the visible spectral region, such as metalhalide doped gas discharge lamps.

In order to compensate for this deficiency, published European Patent Application No. 102,586 describes photoinitiators comprising 1,3-diaza-9-thiaanthracene-2,4-diones, the absorption range and initiating activity of which extend further into the visible spectral region. These compounds are comparatively easily prepared, but they require a reaction step using an aromatic thiol, in which obnoxious odors are emitted so that special protective measures are necessary. Due to the structure of their parent substance, the compounds also tend to have a limited solubility in many solvents and, consequently, their applicability is restricted.

SUMMARY OF THE INVENTION

It is therefore an object of the present inventioin to provide a photopolymerizable composition comprising a photoinitiator that has a activity as high as that of the known photoinitiators, even in the short-wave visible spectral region, but that also can be synthesized without reaction steps in which unpleasant smells are developed, and that has an improved solubility and compatibility with other components of the photopolymerizable composition.

In accomplishing the foregoing object, there has been provided, in accordance with one aspect of the present invention, a photopolymerizable composition comprising
(a) a polymeric binder,
(b) a polymerizable compound comprising at least two terminal, ethylenically unsaturated groups and having a boiling point above 100° C., and
(c) a specific trinuclear N-heterocyclic compound as the photoinitiator.

The photoinitiator compound of the present invention is represented by formula I:

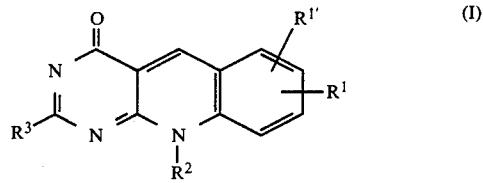

wherein
$R^1$ denotes a hydrogen atom, a halogen atom, an alkyl group, alkoxy group, or dialkylamino group
$R^{1'}$ denotes a hydrogen atom, a halogen atom or an alkyl group,
$R^2$ denotes an alkyl group or an alkoxycarbonylalkyl group, or, if $R^1$ and $R^2$ each denote an alkyl moiety, $R^1$ and $R^2$ together form a five- or six-membered ring, and
$R^3$ denotes an aliphatic or a cycloaliphatic tertiary amino group.

Other objects, features, and advantages of the present invention will become apparent from the following detailed description. It should be understood, however, that the detailed description and specific examples, while indicating preferred embodiments of the invention, are given by way of illustrated only, since various changes and modifications within the spirit and scope of the invention will become apparent to those skilled in the art from this detailed description.

DETAILED DESCRIPTION OF THE PREFERRED EMBODIMENTS

Compounds corresponding to formula I are known from German Offenlegungsschrift No. 3,233,604, where they are described as antimycotically and antibacterially active intermediate products for use in the preparation of similarly acting nitrogen bases which are quaternary in the 10-position. Other uses are not mentioned in this publication.

According to the present invention, it has been found that formula I compounds, when irradiated in the spectral region from about 400 to 450 nm, act as active radical starters of the photopolymerization of vinyl compounds, even in the presence of oxygen. The novel photoinitiators do not initiate thermal polymerization of such vinyl compounds when there is no actinic radiation. Therefore, they are very well suited for the preparation of storable copying layers.

If, in formula I, $R^1$ and $R^{1'}$ are alkyl groups, these groups preferably have from 1 to 4 carbon atoms. When $R^1$ is an alkoxy group or dialkylamino group, it also preferably has alkyl groups containing from 1 to 4, particularly 1 or 2, carbon atoms. The preferred halogen atoms comprise fluorine, chlorine, and bromine, in particular, fluorine and chlorine. $R^{1'}$ preferably is a hydrogen atom. Preferred compounds corresponding to formula I include those isomers in which $R^1$ or, if $R^{1'}$ does not stand for a hydrogen atom, one of the radicals $R^1$ and $R^{1'}$, is in the 7-position of the triazaanthracenone. If $R^1$ and $R^2$ are linked together to form a ring, $R^1$ preferably is in the 9-position. The alkylene chain formed by the two radicals then has 2 or 3 members and may be branched. $R^2$ preferably is an alkyl group having from 1 to 8, in particular from 1 to 4, carbon atoms. If $R^2$ is an alkoxycarbonylalkyl group, it preferably has an alkoxycarbonyl group containing from 2 to 4 carbon atoms and an alkyl group containing from 1 to 4 carbon atoms.

The tertiary amino group $R^3$ is either a dialkylamino group or an alkylcycloalkylamino group having from 1 to 8, preferably from 1 to 4, carbon atoms in each of the alkyl groups and from 5 to 8 carbon atoms in the cycloalkyl group. Alternatively, it can be a completely or partially hydrogenated N-heterocyclic group, for example, a pyrrolidino group, a piperidino group, a hexamethyleneimino group, a morpholino group, a piperazino group, a N-formyl-piperazino group, a N-methylpiperazino group, or a N-phenyl-piperazino group.

The amount of photoinitiators added to the photopolymerizable composition of the present invention in general varies between 0.01 and 10% by weight, preferably between 0.1 and 5% by weight, relative to the non-volatile components of the photopolymerizable composition.

Photopolymerizable monomers suitable for use in the present invention are known and are, for example, described in U.S. Pat. No. 2,760,863 and No. 3,060,023, the contents of which are incorporated herein by reference. Preferred examples are acrylic and methacrylic acid esters of dihydric or polyhydric alcohols, such as diglycerol diacrylate, polyethylene glycol dimethylacrylate, acrylates and methacrylates of trimethylol ethane, trimethylol propane and pentaerythritol; and of polyhydric alicyclic alcohols. Reaction products of diisocyanates with partial esters of polyhydric alcohols are also used advantageously. Monomers of this kind are described in German Offenlegungsschriften No. 2,064,079, No. 2,361,041 and No. 2,822,190. The proportion of monomers contained in the layer in general varies between 10 and 80, preferably 20 and 60, percent by weight.

A great number of soluble organic polymers may be employed as binders. Examples are: polyamides, polyvinyl esters, polyvinyl acetals, polyvinyl ethers, epoxide resins, polyacrylic acid esters, polymethacrylic acid esters, polyesters, alkyd resins, polyacrylamide, polyvinyl alcohol, polyethylene oxide, polydimethyl acrylamide, polyvinyl pyrrolidone, polyvinylmethyl formamide, polyvinylmethyl acetamide, and copolymers of the monomers which form the aforementioned homopolymers.

Other possible binders are natural substances or modified natural substances, for example, gelatin or cellulose ethers.

With particular advantage, binders are used which are insoluble in water, but soluble or at least swellable in aqueous-alkaline solutions, since layers containing such binders can be developed with the preferably employed aqueous-alkaline developers. Binders of this type can, for example, contain the following groups: —COOH, —PO$_3$H$_2$, —SO$_3$H, —SO$_2$NH—, —SO$_2$—NH—SO$_2$— and —SO$_2$—NH—CO—.

Examples of these are: maleic resins, polymers of β-methacryloyloxy-ethyl N-(p-tolyl-sulfonyl)-carbamate and copolymers of these and similar monomers with other monomers, and also styrene/maleic acid anhydride copolymers. Preferably used are copolymers of alkylmethacrylates and methacrylic acid and copolymers of methacrylic acid, alkylmethacrylates and methyl methacrylates and/or styrene, acrylonitrile, and the like, which are described in German Offenlegungsschriften No. 2,064,080 and No. 2,363,806.

In general, the added quantity of binder amounts of 20 to 90% by weight, preferably 40 to 80% by weight, of the layer constituents.

Depending on their intended use and desired properties, the photopolymerizable compositions can contain various additional substances. Examples of these admixtures are:

inhibitors to prevent thermal polymerization of the monomers,
hydrogen donors,
substances regulating the sensitometric properties of layers of this type,
dyes,
colored and uncolored pigments,
color precursors,
indicators,
plasticizers, etc.

These constituents advantageously should be selected to minimize absorption in the region of actinic radiation, which is important for the initiation process.

Within the scope of the present invention, "actinic radiation" is to be understood as denoted any radiation with the energy corresponding at least to that of shortwave visible light. Longwave UV-radiation, electron emission, X-rays, and laser radiation are suitable.

The photopolymerizable composition of the present invention can be used in many applications, such as in the production of safety glass, in varnishes which are hardened by the action of light or corpuscular radiation, such as electron beams, in dental fillings, and, in particular, in a light-sensitive copying material used for reproduction.

The following detailed description of the present invention is directed to the last-mentioned application, but does not limit the present invention thereto. Examples of possible applications in this field are: copying layers for the photomechanical production of printing plates suitable for relief printing, lithographic printing, gravure printing, and screen printing; relief copies, for example, in the production of Braille books; single copies; tanned images; and pigment images. The compositions can further be employed for the photomechanical production of etch resists, for example, for name plates, printed circuits, and chemical milling. The compositions of the present invention are of particular importance with regard to the photomechanical production of lithographic printing plates and etch resists, especially in the form of presensitized materials.

The composition can be used industrially for the above mentioned applications as a liquid solution or dispersion, such as a photoresist solution, which is applied by the consumer to an appropriate support, for example, for chemical milling, for the production of printed circuits, and for screen printing stencils. The composition can also be present as a solid lightsensitive layer on a suitable support, i.e., as a storable, presensitized copying material, for example, for the production of printing plate. It can also be employed for the production of dry resists.

It is in general advantageous substantially to isolate the compositions from the influence of atmospheric oxygen during light polymerization. If the composition is used in the form of thin copying layers, it is recommended to apply a suitable cover film which has a low permeability to oxygen. The cover film may be self-supporting and be removed from the copying layer prior to development. Polyester films, for example, are suitable for this purpose. The cover film may also comprise a material which dissolves in the developer liquid or which can be removed at least from the non-hardened areas during development. Examples of materials suitable for this purpose include waxes, polyvinyl alcohol, polyphosphates, and sugars.

Layer supports which are suitable for copying materials prepared using the composition of the present invention include, for example, aluminum, steel, zinc, copper, plastic films, such as films of polyethylene terephthalate or cellulose acetate, and screen printing supports, such as perlon gauze.

Light-sensitive materials employing the composition of the present invention can be prepared using conventional techniques. Thus, the composition can be taken up in solvent, the resulting solution or dispersion applied to the intended support as a thin film by casting, spraying, immersion, or roller application; and the film subsequently dried. Thick layers (for example, of 250 μm and thicker) are advantageously prepared by first producing a self-supporting film by extrusion or molding, which is then optionally laminated to the support. In the case of dry resists, solutions of the composition are applied to transparent intermediate supports and dried. The light-sensitive layers, having a thickness between about 10 and 100 μm, are then also bonded to the desired support by lamination, along with the temporary support.

The copying materials can be processed using known methods. They are developed by treatment with an appropriate developer solution, preferably a weakly alkaline aqueous solution, whereby the unexposed areas of the layer are dissolved away and the exposed areas of the copying layer remain on the support.

The following examples illustrate the photopolymerizable composition of the present invention. First, the production of a number of novel photoinitiators according to the invention is described. In the following description, parts by weight (p.b.w.) and parts by volume (p.b.v.) are related as g:cm$^3$. Unless otherwise indicated, percentages and quantitative ratios are to be understood as denoting units by weight. The compounds according to the present invention are prepared as specified in Scheme 1, $R^1$, $R^{1'}$, $R^2$, and $R^3$ having the above-indicated significance.

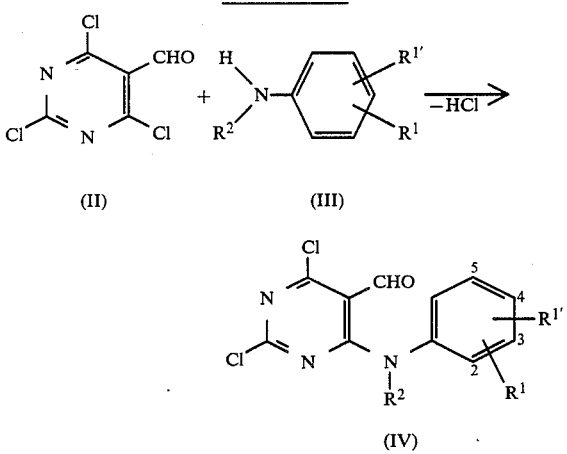

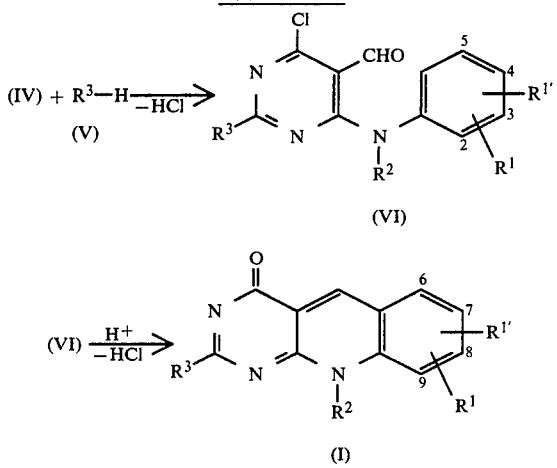

Equimolar quantities of 2,4,6-trichloropyrimidine-5-carbaldehyde according to formula II and a secondary aromatic amine according to formula III are reacted in a solvent which is inert under the conditions of reaction, for example, benzene, diethylether, dioxane, tetrahydrofuran or toluene, preferably tetrahydrofuran, at a temperature between 0° C. and 30° C., in the presence of an acid-binding compound, such as a tertiary amine, pyridine, alkali metal and alkaline earth metal carbonate and hydrogencarbonate, preferably triethylamine, to produce a compound according to formula IV.

When a compound according to formula IV, appropriately with 1.0 to 1.1 equivalents of a secondary amine according to formula V, is reacted in one of the solvents specified above for the preparation of IV, and in the presence of the above-described acid-binding compounds at a temperature between −50° C. and −20° C., a compound according to formula VI is formed which may be isolated, but is preferably further reacted without being isolated first.

The compounds according to formula VI are heated at 70° C. to 150° C. in concentrated sulfuric acid, until the generation of HCl ceases. Following hydrolysis, impurities resulting from side reactions can be removed by filtration. By neutralizing with alkali metal hydroxide, the pure compound I is then precipitated from its solution in dilute sulfuric acid.

This reaction can also be run in polyphosphoric acid at 110° C. to 160° C., or in a mixture of trifluoroacetic acid and sulfuric acid at 40° C. to 50° C., but then reaction times are considerably longer.

The above-summarized preparation process is described in detail below with reference to compound 7 and the starting materials thereof. All stages of the process are representative of a number of corresponding reactions, the results of which are compiled in Tables 1 to 3.

COMPOUND NO. 7

7-chloro-2-diethylamino-10-ethyl-4,10-dihydro-1,3,10-triazaanthracen-4-one 27.3 g (0.074 mole) of 4-chloro-6-(4-chloro-N-ethylanilino)-2-diethylamino-pyrimidine-5-carbaldehyde were added to 550 ml of sulfuric acid (96% strength) at a temperature of 85° C. The resulting mixture was heated at 130° C., until the generation of HCl ceased, and was then poured onto 3 l of ice, filtered and adjusted to a pH of 5 by means of sodium hydroxide. After cooling, the precipitated solid was filtered off by suction. Recrystallization from 150 ml of ethanol yielded 15.5. g of yellow crystals.

(0.127 mole) of triethylamine in 80 ml of tetrahydrofuran was added dropwise to a solution of 40.0 g (0.121 mole) of 6-(4-chloro-N-ethylanilino)-2,4-dichloropyrimidine-5-carbaldehyde in 400 ml of tetrahydrofu-

TABLE 1

| Compound No. | $R^{1'}$ | $R^1$ | $R^2$ | $R^3$ | Melting Point (°C.) | Yield % |
|---|---|---|---|---|---|---|
| 1 | H | H | $C_2H_5$ | $-N(C_2H_5)_2$ | 229–231 | 32.9 |
| 2 | H | 7-$CH_3$ | $C_2H_5$ | $-N(C_2H_5)_2$ | 193–195 | 15.8 |
| 3 | H | 7-$CH_3$ | $C_2H_5$ | pyrrolidin-1-yl | 295 Dec. | 31.5 |
| 4 | 7-$CH_3$ | 8-$CH_3$ | $C_2H_5$ | $-N(C_2H_5)_2$ | 250 Dec. | 27.8 |
| 5 | H | (9)-$CH_2CH_2CH_2-$ | | $-N(C_2H_5)_2$ | 215 Dec. | 3.2 |
| 6 | H | 7-F | $C_2H_5$ | 4-methylpiperazin-1-yl | 217 Dec. | 26.4 |
| 7 | H | 7-Cl | $C_2H_5$ | $-N(C_2H_5)_2$ | 241–242 | 63.1 |
| 8 | H | 7-Cl | $C_2H_5$ | $-N(C_4H_9)_2$ | 225–227 | 41.3 |
| 9 | H | 7-Cl | $C_2H_5$ | piperidin-1-yl | 305 Dec. | 21.4 |
| 10 | H | 7-Cl | $C_2H_5$ | piperazin-1-yl (NH) | 250 Dec. | 66.5 |
| 11 | H | 7-Cl | $C_2H_5$ | 4-methylpiperazin-1-yl | 240–242 | 49.6 |
| 12 | H | 7-Cl | $C_2H_5$ | morpholin-4-yl | 295 Dec. | 54.0 |

4-chloro-6-(4-chloro-N-ethyl-anilino)-2-diethylaminopyrimidine-5-carbaldehyde $R^1$=4-Cl, $R^{1'}$=H, $R^2$=$C_2H_5$, $R^3$=-N($C_2H_5$)$_2$  Formula VI Over five hours, at a temperature of −30° C., a solution of 9.28 g (0.127 mole) of diethylamine and 12.84 g ran. The solution was then stirred for four hours at −30° C. and for two hours at 20° C., the triethylammoniumchloride was filtered off, and the filtrate evaporated in vacuo. After the filtrate was mixed by stirring with 120 ml of diethylether, 27.3 g of colorless crystals were obtained.

TABLE 2

| $R^{1'}$ | $R^1$ | $R^2$ | $R^3$ | Melting Point (°C.) | Yield (%) |
|---|---|---|---|---|---|
| H | H | $C_2H_5$ | $-N(C_2H_5)_2$ | | used as the crude reaction product |
| H | 4-$CH_3$ | $C_2H_5$ | pyrrolidin-1-yl | | used as the crude reaction product |
| 3-$CH_3$ | 4-$CH_3$ | $C_2H_5$ | $-N(C_2H_5)_2$ | | used as the crude reaction product |
| H | (2)-$CH_2CH_2CH_2-$ | | $-N(C_2H_5)_2$ | | used as the crude reaction product |

TABLE 2-continued

| R¹' | R¹ | R² | R³ | Melting Point (°C.) | Yield (%) |
|---|---|---|---|---|---|
| H | 4-F | C₂H₅ | —N⟨ ⟩N—CH₃ | used as the crude reaction product | |
| H | 4-Cl | C₂H₅ | —N(C₂H₅)₂ | used as the crude reaction product | |
| H | 4-Cl | C₂H₅ | —N(C₂H₅)₂ | 93–95 | 61.4 |
| H | 4-Cl | C₂H₅ | —N⟨ ⟩O | 142–144 | 62.2 |
| H | 4-Cl | C₂H₅ | —N⟨ ⟩N—CH₃ | used as the crude reaction product | |
| H | 4-Cl | C₂H₅ | —N⟨ ⟩N—CHO | 182–185 | 41.6 |

6-(4-chloro-N-ethyl-anilino)-2,4-dichloro-pyrimidine-5-carbaldehyde $R^1 = 4\text{-Cl}, R^{1'} = H, R^2 = C_2H_5$   Formula IV Solutions of 15.56 g (0.1 mole) of 4-chloro-N-ethylaniline (III) and 11.13 g (0.11 mole) of triethylamine, in each case in 50 ml of tetrahydrofuran, were successively added dropwise to a solution of 21.14 g (0.1 mole) of 2,4,6-trichloropyrimidine-5-carbaldehyde (II) in 100 ml of tetrahydrofuran. The solution was then stirred for three hours at room temperature and the triethylammoniumchloride was filtered off. The filtrate was then evaporated in vacuo and stirred with 150 ml of methanol at 0° C. 23.9 g of colorless crystals were obtained.

TABLE 3

| R¹' | R¹ | R² | Melting Point (°C.) | Yield (%) |
|---|---|---|---|---|
| H | H | CH₃ | 104–106 | 59.2 |
| H | H | C₂H₅ | 117–118 | 39.0 |
| H | 2-CH₃ | CH₃ | 82–84 | 33.3 |
| H | 4-CH₃ | C₂H₅ | 127–130 | 44.5 |
| 3-CH₃ | 4-CH₃ | C₂H₅ | 125–127 | 59.1 |
| H | (2)-CH₂CH₂— | | 163–165 | 40.6 |
| H | (2)-CH₂CH₂CH₂— | | 143–146 | 72.2 |
| H | 2-OCH₃ | C₂H₅ | 95 Dec. | 42.9 |
| H | 4-OCH₃ | C₂H₅ | 100–103 | 78.5 |
| H | 4-F | C₂H₅ | 132–133 | 71.3 |
| 3-Cl | 4-Cl | C₂H₅ | 153–156 | 30.1 |
| H | 4-Cl | C₂H₅ | 138–139 | 72.3 |

EXAMPLE 1

Coating solutions were prepared which contained

| | |
|---|---|
| 4.7 p.b.w. | of a copolymer composed of 95% of methylmethacrylate and 5% of dimethylaminoethylmethacrylate and having an average molecular weight M_w of about 40,000, |
| 3.3 p.b.w. | of trimethylolpropane triacrylate, |

-continued

| | | |
|---|---|---|
| | 0.05 p.b.w. | of leuco crystal violet, |
| | 0.02 p.b.w. | of 1,4-bis-(4-tert-butoxy-phenylamino)-5,8-dihydroxyanthraquinone, |
| | and the following photoinitiators: | |
| (a) | 0.1 p.b.w. | of compound 2 |
| (b) | 0.1 p.b.w. | of compound 4 |
| (c) | 0.1 p.b.w. | of compound 8 |
| (d) | 0.03 p.b.w. | of compound 9, respectively, |
| | 19 p.b.w. | of butanone. |

The solutions were spin-coated upon 23 μm thick, biaxially stretched and heat-set polyethylene terephthalate films, such that layer weights of 38 g/m² were obtained after drying at 100° C.

A commercial laminating device was used to laminate each dry resist film thus prepared at 120° C. to a phenoplast laminate clad with a 35 μm thick copper foil. The dry resist films were then exposed for 40 seconds to the light of a 5 kW metal halide lamp arranged at a distance of 110 cm from the vacuum copying frame. A 13-step exposure wedge with density increments of 0.15 and a line original having line widths and line spaces to 80 μm were used as the original in each case.

After exposure, the polyester films were peeled off and the layers were developed during 20 seconds in a spray developing apparatus, using 1,1,1-trichloroethane.

The numbers of fully cross-linked wedge steps obtained were as follows:

(a)=4; (b)=3; (c)=5; and (d)=5.

EXAMPLE 2

The polyester films indicated in Example 1 were spin-coated with solutions of the following compositions, such that after drying a layer weight of 40 g/m² was obtained in each case:

| | | |
|---|---|---|
| (a) | 4.7 p.b.w. | of the copolymer described in Example 1, |

-continued

| | | |
|---|---|---|
| | 3.3 p.b.w. | of trimethylolpropane triacrylate, |
| | 0.5 p.b.w. | of leuco crystal violet, |
| | 0.02 p.b.w. | of the green anthraquinone dye of Example 1, and |
| | 0.05 p.b.w. | of compound 7 in |
| | 19 p.b.w. | of butanone; |
| (b) | | a solution as in (a), but with the addition of |
| | 0.075 p.b.w. | of ethyl-4-dimethylaminobenzoate. |

The resulting dry resist films were laminated, exposed and developed as described in Example 1. Layer (a) yielded 6 fully cross-linked wedge steps and layer (b) 8 (9) fully cross-linked wedge steps, the figure in brackets indicating the number of fully cross-linked steps plus ghost steps.

The developed plates were rinsed with tap water for 30 seconds, slightly etched in a 15% strength solution of ammonium peroxydisulfate for 30 seconds, again rinsed with water, immersed in a 10% strength sulfuric acid for 30 seconds, and then successively electroplated in the following electrolyte baths:

(1) 45 minutes in a copper electrolyte bath, type "Glanzkupfer-Bad," manufactured by Schloetter, Geislingen/Steige, Federal Republic of Germany,
current density: 2.5 A/dm$^2$
metal build-up: about 22 μm
temperature: room temperature, and
(2) 15 minutes in a nickel bath, type "Norma," manufactured by Schloetter, Geislingen/Steige
current density: 3.5 A/dm$^2$
metal build-up: 10 μm
temperature: 50° C.;
or
(1) copper-plating as described above, and
(2) 20 minutes in a lead-tin bath LA, manufactured by Schloetter, Geislingen/Steige
current density: 1.5 A/dm$^2$
metal build-up: 20 μm
temperature: room temperature
The plates obtained did not show any undercutting or damage.

EXAMPLE 3

The resist films described in Example 2 were each laminated to a cleaned support comprising an insulating material provided with a 35 μm thick copper layer. The boards thus prepared were exposed for 40 seconds through an original of a circuit diagram and then developed with 1,1,1-trichloroethane. The bared copper was removed by etching with an ammonia/cupric chloride solution (pH 8.5) at 48° C. to 50° C. The resist layers showed an excellent resistance to the etching medium used.

EXAMPLE 4

The following coating solution was used to prepare a dry resist film:

| | | |
|---|---|---|
| | 4.7 p.b.w. | of a copolymer composed of 98% of methylmethacrylate and 2% of methacrylic acid and having an average molecular weight M$_w$ of about 35,000, |
| | 3.3 p.b.w. | of trimethylolpropane triacrylate, |
| | 0.5 p.b.w. | of leuco crystal violet, |
| | 0.02 p.b.w. | of the anthraquinone dye of Example 1, |
| | 0.05 p.b.w. | of compound 7, and |
| | 0.125 p.b.w. | of ethyl-4-dimethylaminobenzoate in |
| | 14 p.b.w. | of butanone. |

The dry layer weight of the resulting film was adjusted to 36 g/m$^2$. The material was processed as described in Example 1. Nine fully cross-linked wedge steps were obtained.

EXAMPLE 5

A solution of

| | | |
|---|---|---|
| | 6.0 p.b.w. | of a terpolymer composed of 78% of butylmethacrylate, 20% of methylmethacrylate and 2% of methacrylic acid and having an average molecular weight M$_w$ of about 30,000, |
| | 2.0 p.b.w. | of trimethylolpropane triacrylate, |
| | 0.05 p.b.w. | of leuco crystal violet, |
| | 0.02 p.b.w. | of the anthraquinone dye of Example 1, |
| | 0.05 p.b.w. | of compound 7, and |
| | 0.15 p.b.w. | of ethyl-4-dimethylaminobenzoate in |
| | 14 p.b.w. | of butanone | was spin-coated upon a polyester film, such that a dry layer weight of 69 g/m$^2$ was obtained. The layer was processed as described in Example 1. Eight (9) cross-linked wedge steps were obtained.

EXAMPLE 6

The following coating solutions were prepared:

| | | |
|---|---|---|
| | 4 p.b.w. | of a styrene-maleic anhydride copolymer partially esterified with an alkanol and having an average molecular weight M$_w$ of about 20,000 and an acid number of about 200, |
| | 4 p.b.w. | of a diurethane, prepared from 2 moles of glycerol dimethacrylate and 1 mole of hexamethylene diisocyanate, |
| | 0.14 p.b.w. | of a blue azo dye, obtained by coupling 2,4-dinitro-6-chloro-benzenediazonium salt with 2-methoxy-5-acetylamino-N—cyanoethyl-N—hydroxyethylaniline, |
| | | and the following photoinitiators: |
| (a) | 0.21 p.b.w. | of compound 10 or |
| (b) | 0.25 p.b.w. | of compound 11 in |
| | 70 p.b.w. | of butanone, |
| | 40 p.b.w. | of butylacetate, and |
| | 20 p.b.w. | of ethylene glycol monomethyl ether. |

The solutions were spin-coated upon aluminum which had been electrochemically roughened, anodically oxidized to form an oxide layer of 2 g/m$^2$, and pretreated with an aqueous solution of polyvinyl phosphonic acid, such that a dry layer weight of 2 g/m$^2$ was obtained. The plate was then provided with a covering layer of polyvinyl alcohol, having layer weight of 4 g/m$^2$. The resulting printing plate was exposed to the light of a 5 kW metal halide lamp for 160 seconds, under a 13-step continuous tone step wedge.

The printing plate was then developed with a developer having the following composition:

| | | |
|---|---|---|
| | 3.0 p.b.w. | of sodium metasilicate $\times$ 9 H$_2$O, |
| | 0.03 p.b.w. | of a nonionic wetting agent (coconut fatty alcohol-polyoxyethylene ether, having about 8 oxyethylene units), |

| 0.003 p.b.w. | of an anti-foaming agent, and |
| 96.967 p.b.w. | of deionized water. |

The following numbers of cross-linked wedge steps were obtained: 3 (4) in the layer containing photoinitiator (a) and 1 (2) in the layer containing photoinitiator (b)

What is claimed is:

1. A photopolymerizable composition comprising:
   (a) a polymeric binder;
   (b) a polymerizable compound comprising at least two terminal, ethylenically unsaturated groups and having a boiling point above 100° C.; and
   (c) a trinuclear N-heterocyclic photoinitiator compound, said photoinitiator compound being represented by the formula

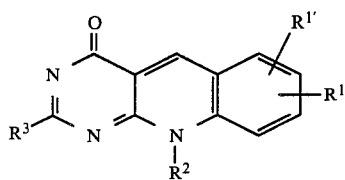

wherein $R^1$ denotes a hydrogen atom, a halogen atom, an alkyl group, an alkoxy group or a dialkylamino group, $R^{1'}$ denotes a hydrogen atom, a halogen atom or an alkyl group, $R^2$ denotes an alkyl group or an alkoxycarbonylalkyl group, or, if $R^1$ and $R^2$ each denote an alkyl moiety, $R^1$ and $R^2$ together form a five- or six-membered ring, and $R^3$ denotes an aliphatic or a cycloaliphatic tertiary amino group.

2. A photopolymerizable composition as claimed in claim 1, wherein $R^3$ denotes a dialkylamino group having from 2 to 16 carbon atoms; an N-alkyl-cycloalkylamino group having from 1 to 4 carbon atoms in the alkyl radical and from 5 to 8 carbon atoms in the cycloalkyl radical; or an N-heterocyclic group formed of 5 to 7 ring members and having from 4 to 10 carbon atoms.

3. A photopolymerizable composition as claimed in claim 1, wherein $R^{1'}$ is a hydrogen atom and $R^1$ is in the 7-position of the ring system of said formula.

4. A photopolymerizable composition as claimed in claim 1, wherein $R^1$ is in the 9-position of the ring system of said formula and, together with $R^2$, forms an ethylene group or a propylene group.

5. A photopolymerizable composition as claimed in claim 1, wherein each of $R^1$ and $R^{1'}$ is an alkyl group containing 1 to 4 carbon atoms.

6. A photopolymerizable composition as claimed in claim 1, wherein $R^1$ is an alkyl group or a dialkylamino group, and comprises an alkyl moiety containing 1 to 4 carbon atoms.

7. A photopolymerizable composition as claimed in claim 1, wherein $R^2$ is an alkyl group containing 1 to 8 carbon atoms.

8. A photopolymerizable composition as claimed in claim 1, wherein $R^2$ is an alkoxycarbonylalkyl group comprising (i) an alkoxycarbonyl moiety which contains 2 to 4 carbon atoms and (ii) an alkyl moiety containing 1 to 4 carbon atoms.

9. A photopolymerizable composition as claimed in claim 1, wherein said polymerizable compound (b) comprises an acrylic or methacrylic acid ester of a polyhydric alcohol.

10. A photopolymerizable composition as claimed in claim 1, wherein said polymeric binder (a) is insoluble in water and soluble in dilute aqueousalkaline solutions.

11. A dry resist film comprising a transparent temporary support layer and a light-sensitive copying layer provided on said temporary support layer, said copying layer comprising a photopolymerizable composition as claimed in claim 1.

12. A dry resist film as claimed in claim 11, wherein said temporary support comprises a polyester film.

13. A printing plate comprising a metal substrate and a light-sensitive copying layer provided on said substrate, said copying layer comprising a photopolymerizable composition as claimed in claim 1.

14. A printing plate as claimed in claim 13, wherein said metal substrate is comprised of a roughened aluminum surface and an anodic oxidation layer provided on said aluminum surface.

* * * * *